United States Patent
Han et al.

(10) Patent No.: US 9,687,163 B2
(45) Date of Patent: Jun. 27, 2017

(54) SEIZURE DETECTION AND EPILEPTOGENIC LESION LOCALIZATION

(71) Applicant: THE REGENTS OF THE UNIVERSITY OF CALIFORNIA, Oakland, CA (US)

(72) Inventors: Yu Han, Quincy, MA (US); Wentai Liu, Los Angeles, CA (US); Yue-Loong Hsin, Hualien (TW)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 865 days.

(21) Appl. No.: 14/067,888

(22) Filed: Oct. 30, 2013

(65) Prior Publication Data

US 2014/0128762 A1 May 8, 2014

Related U.S. Application Data

(63) Continuation of application No. PCT/US2012/036416, filed on May 4, 2012.
(Continued)

(51) Int. Cl.
*A61B 5/04* (2006.01)
*A61B 5/0476* (2006.01)
(Continued)

(52) U.S. Cl.
CPC .......... *A61B 5/04014* (2013.01); *A61B 5/048* (2013.01); *A61B 5/0476* (2013.01);
(Continued)

(58) Field of Classification Search
None
See application file for complete search history.

(56) References Cited

U.S. PATENT DOCUMENTS 6,473,639 B1    10/2002  Fischell et al.
2004/0267152 A1 12/2004 Pineda
(Continued)

FOREIGN PATENT DOCUMENTS

WO    2012/151453 A2   11/2012

OTHER PUBLICATIONS

Zhukov et al. Independent Component Analysis for EEG Source Localization. IEEE Engineering in Medicine and Biology (May/Jun. 2000).*
(Continued)

*Primary Examiner* — Etsub Berhanu
(74) *Attorney, Agent, or Firm* — O'Banion & Ritchey LLP; John P. O'Banion

(57) ABSTRACT

Epileptogenic source localization methods and systems based on ECoG signals are provided for obtaining spatial and temporal relationships among epileptogenic zones. Seizure detection is based on an Independent Component Analysis (ICA) and temporal and spatial relationships among the detected epileptogenic zones are based on a steepest descent-based source localization method. Embodiments of the invention facilitate the epileptiform activity investigation and seizure dynamics study and further benefit the neurophysiology community in the surgical decision making of neurosurgeons.

8 Claims, 11 Drawing Sheets

Related U.S. Application Data

(60) Provisional application No. 61/518,414, filed on May 4, 2011.

(51) Int. Cl.
*A61B 5/048* (2006.01)
*A61B 5/00* (2006.01)

(52) U.S. Cl.
CPC .......... *A61B 5/4064* (2013.01); *A61B 5/4094* (2013.01); *A61B 5/7257* (2013.01)

(56) References Cited

U.S. PATENT DOCUMENTS

| | | | |
|---|---|---|---|
| 2005/0007091 A1* | 1/2005 | Makeig | A61B 5/048 324/76.13 |
| 2005/0071159 A1* | 3/2005 | Boman | G10L 21/0208 704/233 |
| 2008/0183093 A1* | 7/2008 | Duann | A61B 5/04525 600/516 |
| 2009/0316928 A1 | 12/2009 | Seltzer et al. | |
| 2010/0069776 A1 | 3/2010 | Greger et al. | |
| 2010/0217147 A1 | 8/2010 | Odame | |

OTHER PUBLICATIONS

Ventouras et al. Independent Component Analysis for Source Localization of EEG Sleep Spindle Components. Computational Intelligence and Neuroscience, vol. 2010, Article ID 329436.*

Zaveri H. P., et al., "Time-Frequency Representation of Electrocorticograms in Temporal Lobe Epilepsy," IEEE Trans. on Biomed. Eng., 39(5):502-509, 1992.

Korean Intellectual Property Office, International Search Report and Written Opinion issued on Nov. 23, 2012 for corresponding International Patent Application No. PCT/US2012/036416 (published as WO 2012/151453 on Nov. 8, 2012) (pp. 1-8) with claims searched (pp. 9-15) pp. 1-15.

Hyvärinen A. and Oja E., Independent Component Analysis: Algorithms and Applications, Neural Netw. 13:411-430, 2000.

Hyvarinen A. and Oja E., A Fast Fixed-Point Algorithm for Independent Component Analysis, Neural Comput., 9(7):1483-1492, 1997.

* cited by examiner

SEIZURE DETECTION AND EPILEPTOGENIC LESION LOCALIZATION

CROSS-REFERENCE TO RELATED APPLICATIONS

This application is a 35 U.S.C. §111(a) continuation of PCT international application number PCT/US2012/036416 filed on May 4, 2012, incorporated herein by reference in its entirety, which is a nonprovisional of U.S. provisional patent application Ser. No. 61/518,414 filed on May 4, 2011, incorporated herein by reference in its entirety. Priority is claimed to each of the foregoing applications.

The above-referenced PCT international application was published as PCT International Publication No. WO 2012/151453 on Nov. 8, 2012 and republished on Jan. 17, 2013, which publications are incorporated herein by reference in their entireties.

BACKGROUND OF THE INVENTION

1. Field of the Invention

The invention relates to methods and systems for seizure detection and epileptogenic lesion localization.

2. Description of Related Art

Electrocorticography (ECoG) has become a standard tool to record cortical activity for defining seizure-related zones since 1950s. In clinical practice, mapping the resectable epileptogenic zone still relies on reading through the ECoG signals by the epileptologists. Accordingly, there is a need in the art to develop new techniques based on ECoG signals for epileptic seizure detection and source localization to benefit the neurophysiology community in the surgical decision making of neurosurgeons, and would facilitate the epileptiform activity investigation and seizure dynamics study.

3. REFERENCES

[1] Hyvärinen A. and Oja E., Independent Component Analysis: Algorithms and Applications, *Neural Netw.* 13:411-430, 2000.

[2] Hyvarinen A. and Oja E., A Fast Fixed-Point Algorithm for Independent Component Analysis, *Neural Comput.*, 9(7):1483-1492, 1997.

[3] Zaveri H. P., Williams W. J., Iasemidis L. D., and Sackellares J. C., Time-Frequency Representation of Electrocorticograms in Temporal Lobe Epilepsy, *IEEE Trans. on Biomed. Eng.*, 39(5):502-509, 1992.

BRIEF SUMMARY OF THE INVENTION

The present invention provides methods and systems to not only detect a seizure in time, but also identify seizure sources in the cortex and thus facilitate surgeons to make a precise resection of the epileptogenic lesions. In other words, embodiments pertain to epileptogenic source localization for obtaining spatial and temporal relationships among epileptogenic zones.

In general, two techniques are utilized: (1) An Independent Component Analysis (ICA) based seizure detection method, and (2) A steepest descent-based source localization method for determining temporal relationships among the detected seizures. Both the seizure detection and the source localization can be coded in a computer language and the coded computer language can be stored on a computer-readable medium which is then executable by a computing device. In an epileptogenic source localization system for obtaining spatial and temporal relationships among epileptogenic zones, an ECoG data analysis device could be utilized for obtaining a plurality of channels from a subject's brain, which is then used in combination with a computer processor to execute the methods.

The seizure detection method includes preprocessing of ECoG data obtained using a plurality of channels from a subject's brain. The preprocessing removes the mean of the ECoG data and achieves whitening of the ECoG data. The preprocessing is used to uncover Independent Components (ICs) and to estimate a mixing matrix (containing the weights that map the source components (s) onto the recorded signals (x) on the electrode surface). Seizure detection is then performed on each of the uncovered ICs to identify a seizure. The latter steps includes additional processes like the application of a fast Fourier transform (FFT) function to each of the ICs to obtain a frequency spectrum of each of the ICs. Another process is the calculation of a power spectrum for each of the ICs in a frequency band. Yet another process is that based on one or more criteria seizure for each of the ICs is detected and if the seizure is detected a reduced mixing matrix is calculated from the earlier calculated mixing matrix, and a seizure matrix is calculated.

Examples of criteria for detecting a seizure for each of the ICs are: (1) a power spectrum being higher than a predefined threshold, (2) determined by the sampling frequency, a frequency bandwidth of interest, number of points in FFT, and a power scaling factor, (3) a frequency with the largest amplitude or a frequency with the second largest amplitude located within a bandwidth of interest., or (4) any combination thereof.

Continuing in the processing, a back projection is used which includes the calculation of the product of the reduced mixing matrix and the seizure IC matrix, and the calculation of power strength data for each of the plurality of channels.

The localization method includes the selection of p principal paths for each of the seizure ICs by choosing p largest absolute elements from the corresponding column of the reduced mixing matrix. Furthermore, the localization method calculates a principal distance matrix between the plurality channels and the seizure sources. A steepest-descent algorithm is then calculated to position each of the seizure sources according to the principal distance matrix. Finally, a directed transfer function (DTF) is applied to analyze a casual temporal relation among the seizure sources.

The power strength data and temporal relations in any form or way can be displayed or presented to a user of the method or system.

BRIEF DESCRIPTION OF THE SEVERAL VIEWS OF THE DRAWING(S)

Figure 6A:
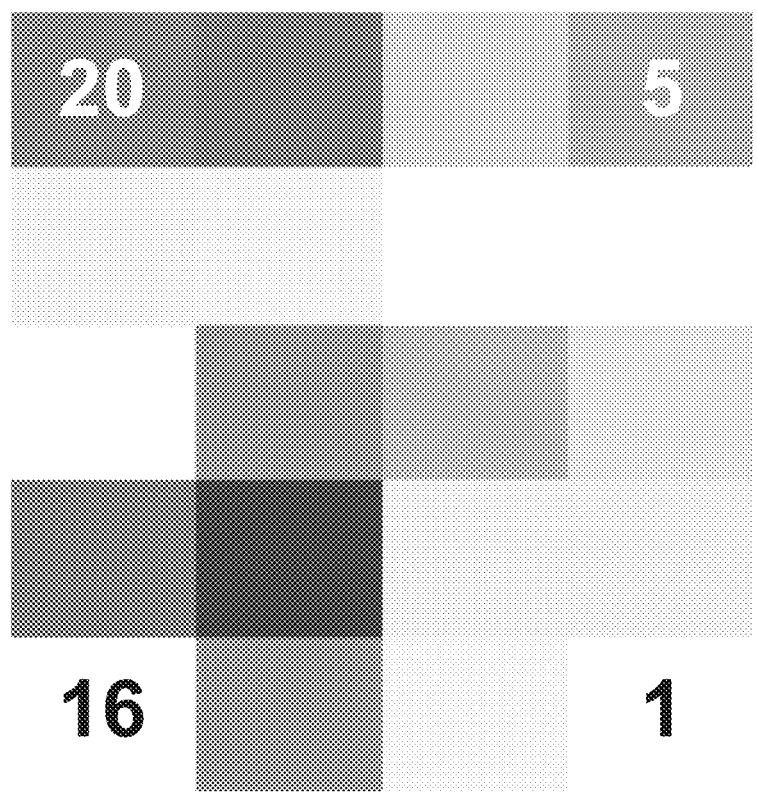
Figure 6B:
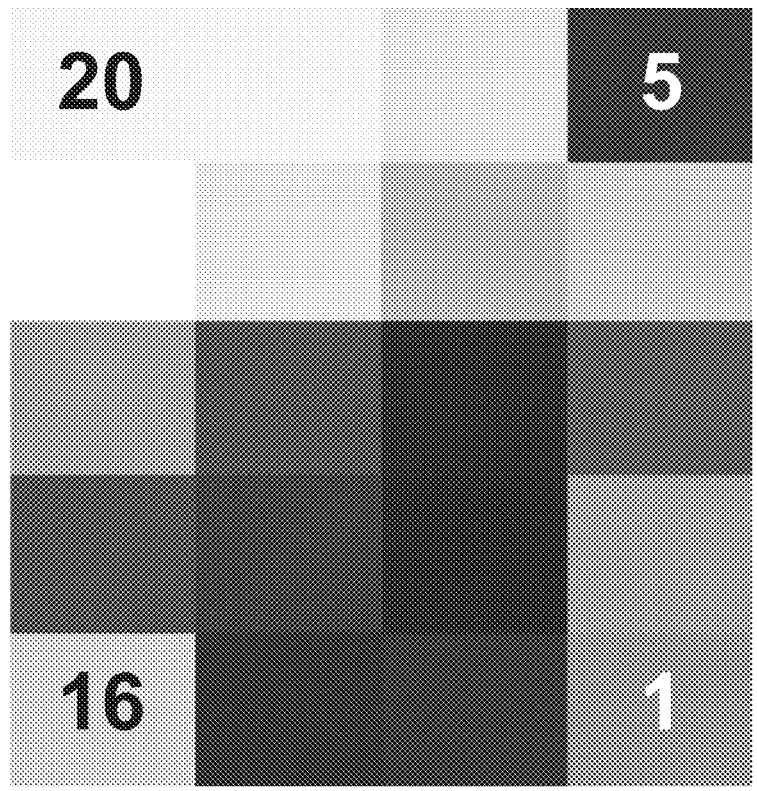

FIGS. 6A-B show examples of power strength diagram of a recording electrode grid according to an exemplary embodiment of the invention. The numbers of 1 to 20 (from bottom right (1) to upper left (20), note only 4 number shown) indicate channels corresponding to those shown in ECoG waveforms. FIG. 6A shows power strengths of signals after back projection. FIG. 6B shows power strengths of original ECoG data.

Figure 7A:
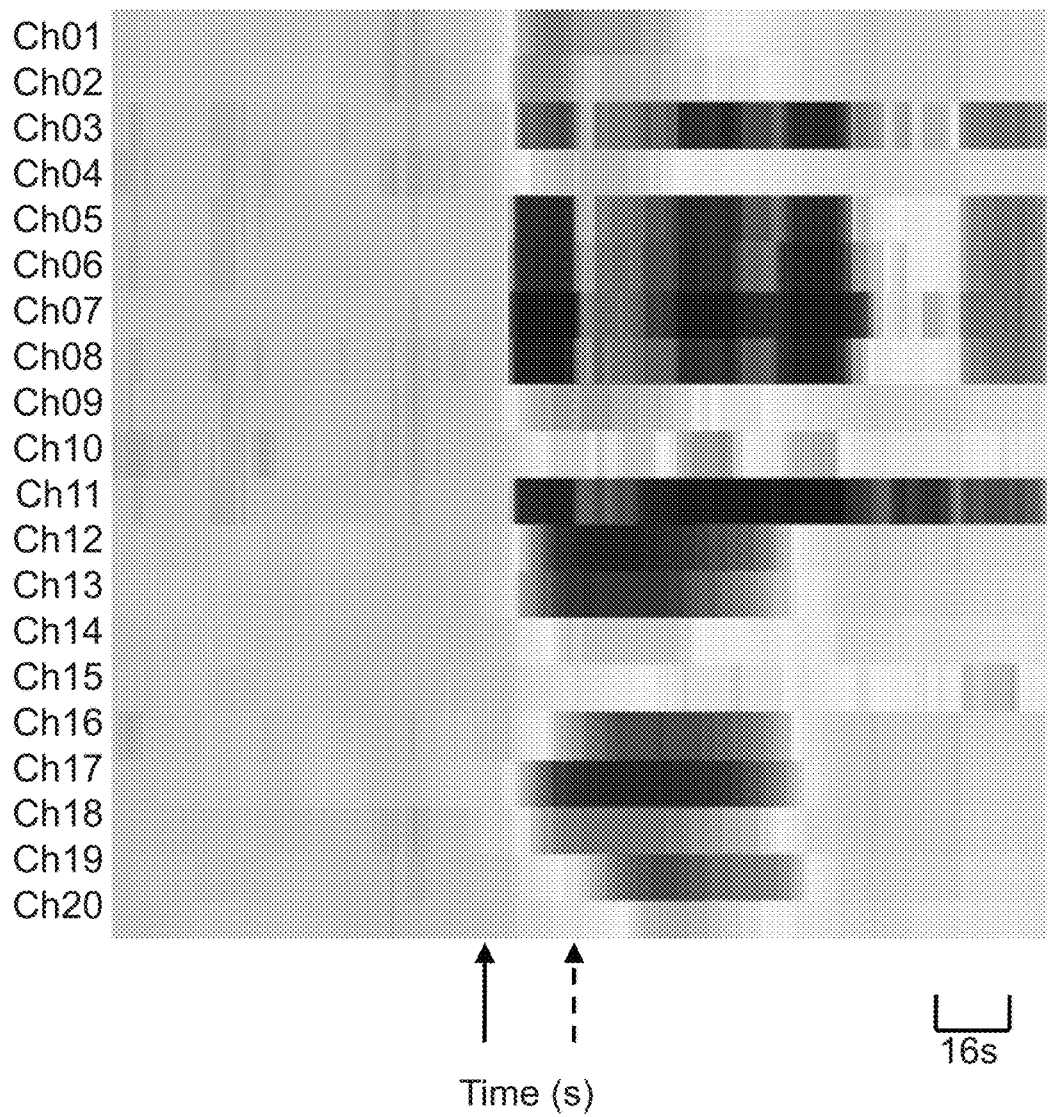
Figure 7B:
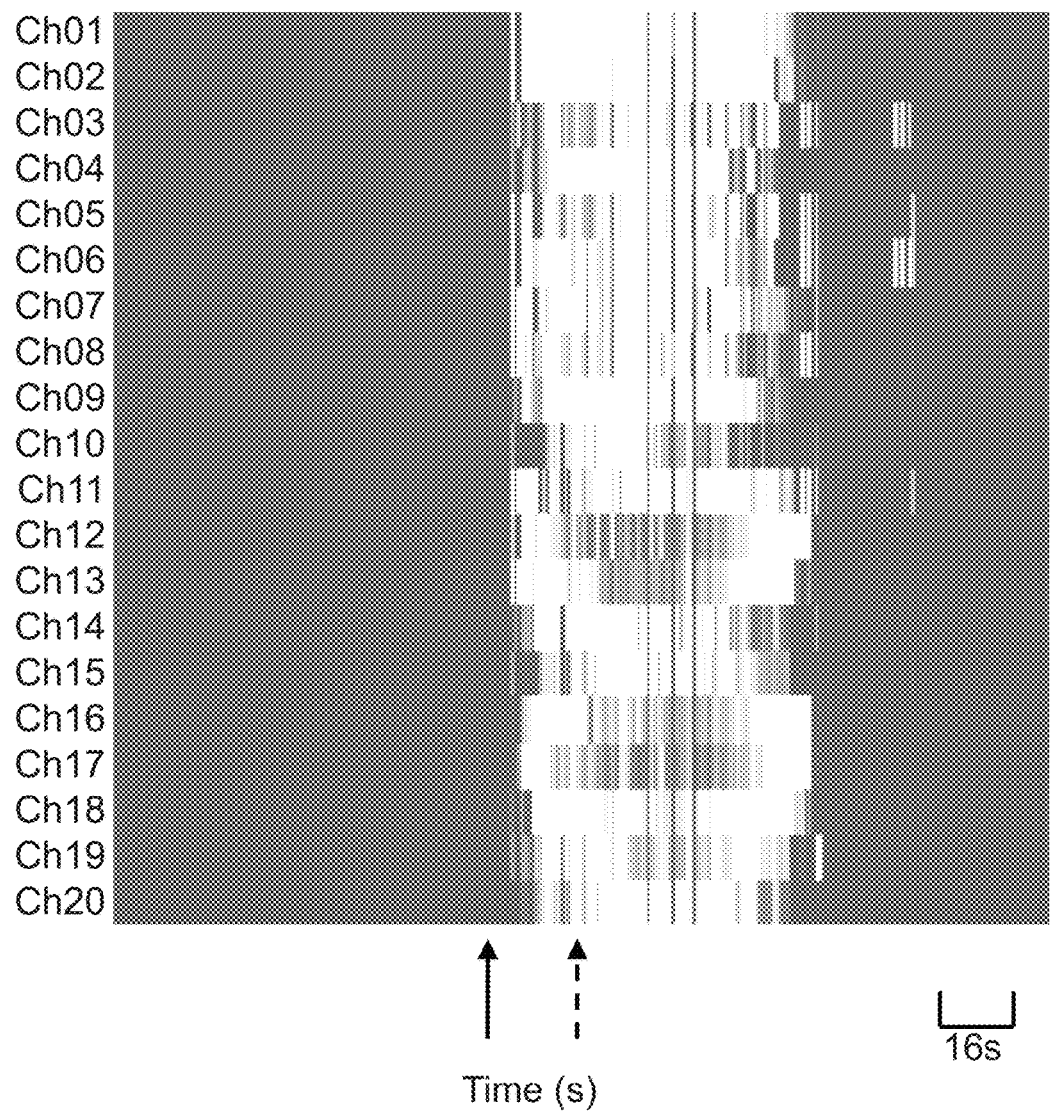

FIGS. 7A-B show examples of power strength diagram changing with time according to an exemplary embodiment of the invention. The black solid arrow indicates the electrographic onset (EO) marked separately by one epileptologist and the dashed arrow indicates the tested epoch of the above example. FIG. 7A shows power strengths of the original ECoG data. FIG. 7B shows power strengths of signals after back projection.

Figure 8A:
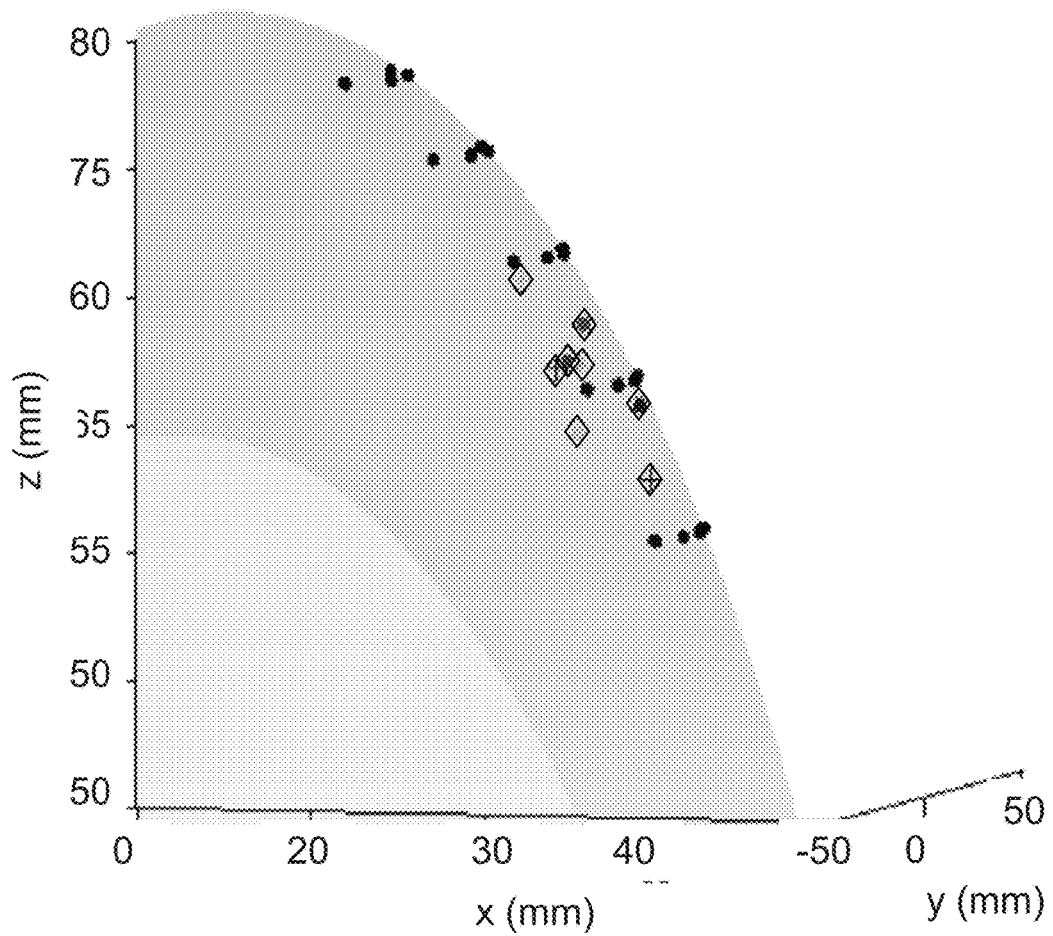
Figure 8B:
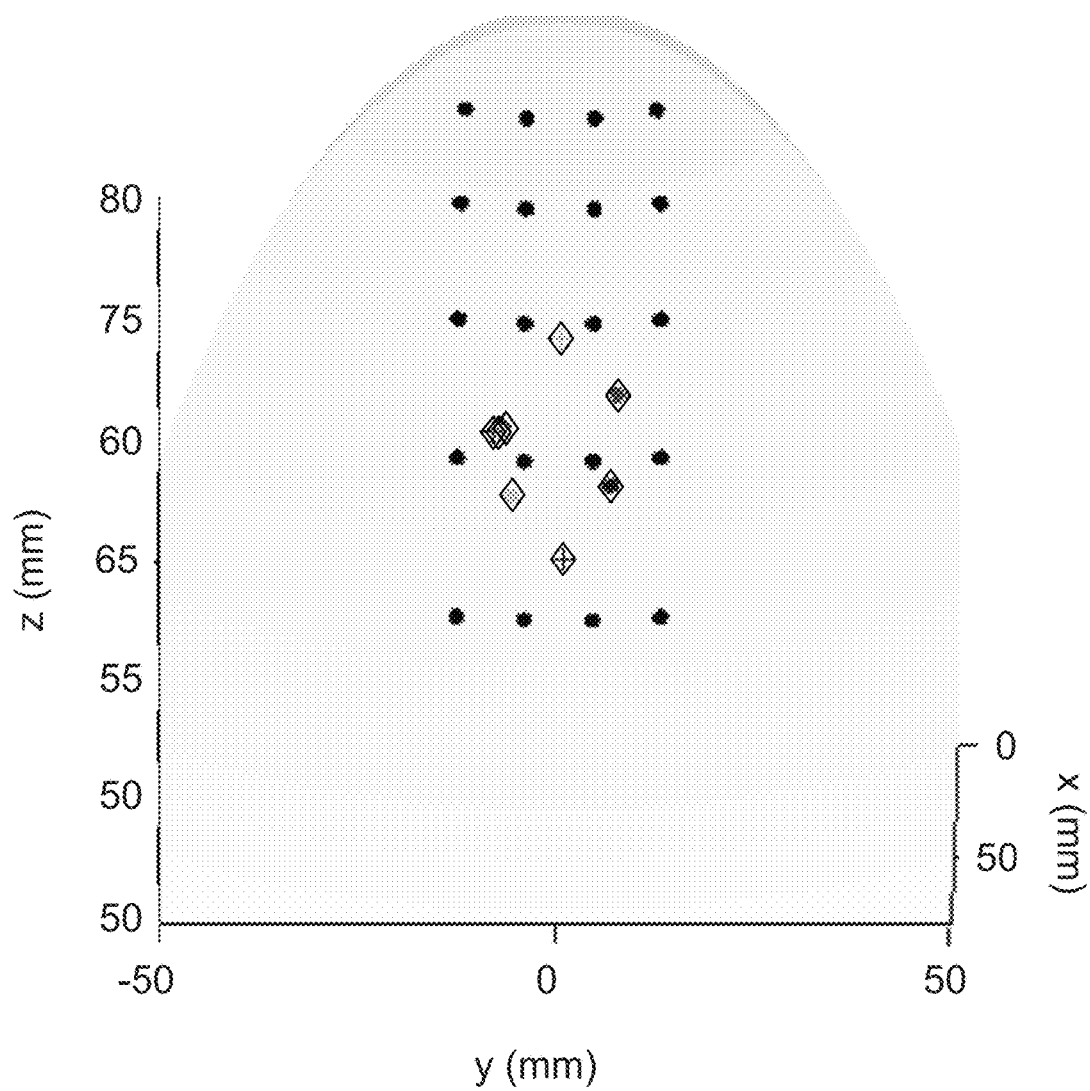

FIGS. 8A-B show examples of localized seizure sources, where the black dots represent the electrodes and the other patterns (inside the diamond shapes) are identified sources. FIG. 8A shows a lateral view. FIG. 8B shows a top view.

DETAILED DESCRIPTION OF THE INVENTION

In this invention an epileptogenic source localization method is provided, which can be practiced as a computer-implemented method, computer code or computer modules executable on a computer. The computer method can be read from a portable on a computer readable medium or stored in flash memory of a computer or on a hard-disk of a computer. The embodiments of the invention can also be integrated or used with hardware and integrated with Electrocochleography (ECoG), Electroencephalography (EEG) devices and systems.

Figure 1:
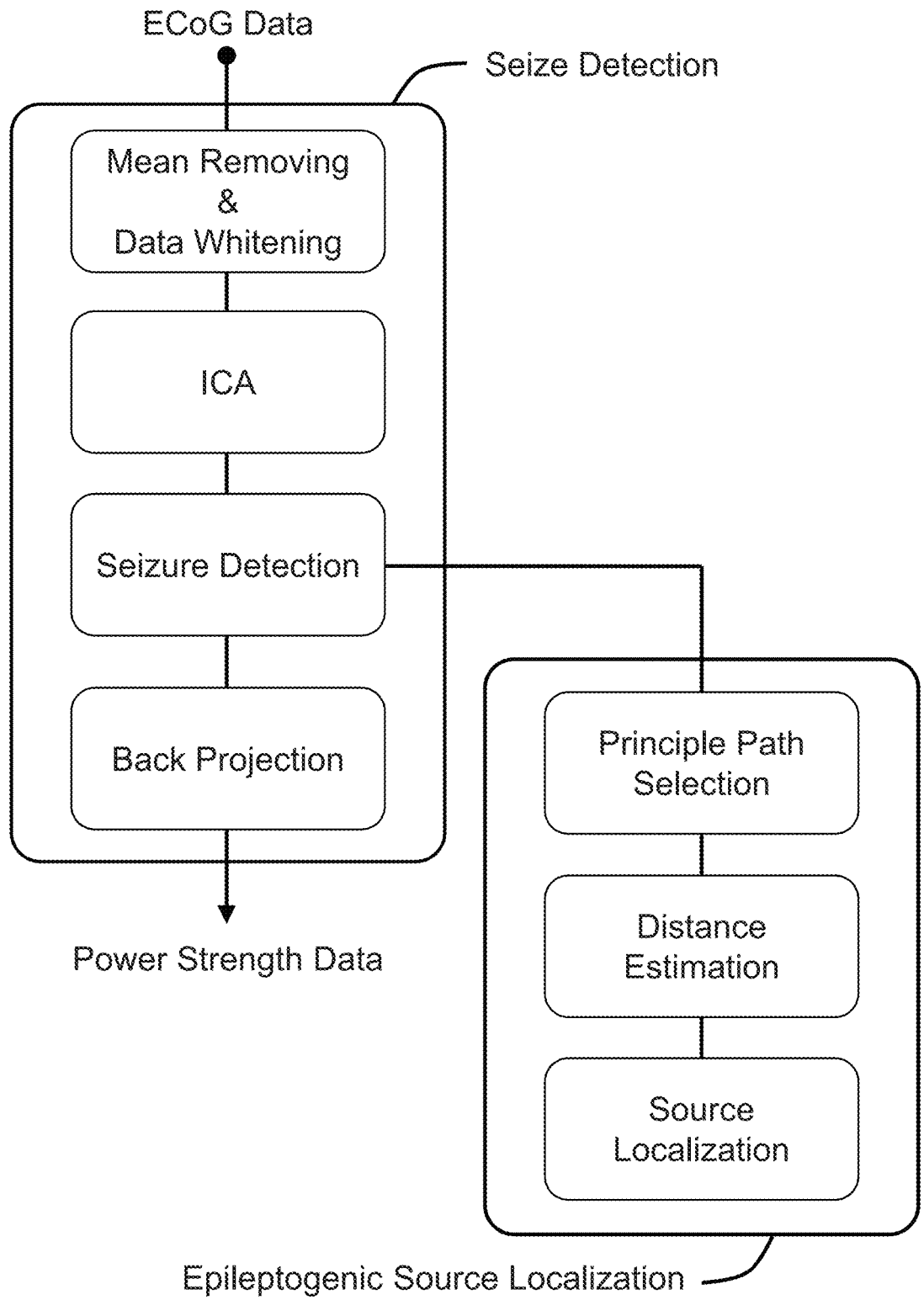
FIG. 1 shows a flow diagram of the seizure detection method and epileptogenic source localization method according to an embodiment of the invention.

The method of the invention as shown in FIG. 1 includes two parts: (1) the Independent Component Analysis (ICA) based seizure detection and (2) the steepest descent based source localization.

Seizure Detection Scheme

Before describing the detection methodology, we first define some of the mathematical notations that build up the algorithm. Denote $x=(x_1^T, x_2^T, \ldots, x_N^T)^T$ the data matrix including N measured channels with $x_i=(x_i(t_1), x_i(t_2), \ldots, x_i(t_L))^T$ the vector representing the temporal sequence of the ith channel, in which the notation T denotes the matrix (or vector) transposition. Denote the underneath source matrix by $s=(s_1^T, s_2^T, \ldots, s_M^T)^T$, where $s_j=(s_j(t_1), s_j(t_2), \ldots, s_j(t_L))^T$ is the jth independent component (IC). By incorporating a mixing matrix A, the data can be modeled as:

$$x = As \qquad (1)$$

where the mixing matrix maps the source space into the data space. Generally, it is assumed that the inverse problem is over-determined which means that the number of sources is smaller than or equal to the number of data channels, i.e. $M \leq N$.

Figure 2:
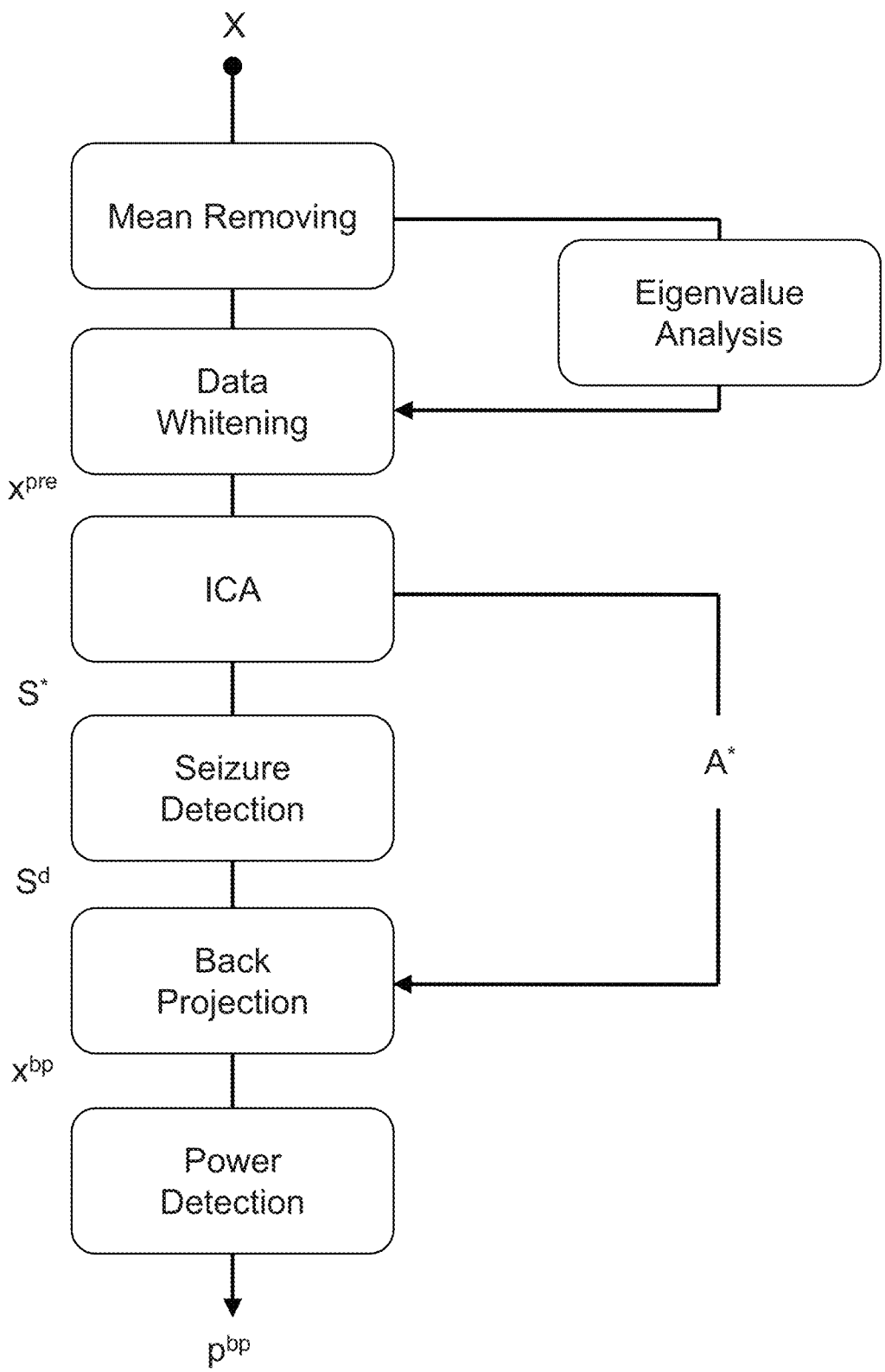
FIG. 2 shows a flow diagram of the seizure detection method according to an exemplary embodiment of the invention.

FIG. 2 shows the procedure of the seizure detection scheme. In the first step, ECoG data x is preprocessed to remove its mean and achieve whitening using eigenvalue analysis to simplify and well-condition subsequent decomposition procedures. The preprocessed data is labeled as $x^{pre}$.

In the second step, a FastICA algorithm [References 1, 2], with fast convergence and no need of statistical prior knowledge, is employed to data $x^{pre}$ to uncover each IC $s_j$ iteratively and to estimate the mixing matrix A in the meanwhile. The decomposed IC matrix s* can be represented as follows:

$$s^* = A^{*-1} x^{pre} \qquad (2)$$

where $A^{*-1}$ is the inverse of the estimated mixing matrix A*. Here the matrix A* can be written as $A^* = (a_1, a_2, \ldots, a_M)$, in which $a_j = (a_{1,j}, a_{2,j}, \ldots, a_{N,j})^T$ represents its jth column corresponding to the decomposed jth IC, and the matrix s* is defined as $s^* = (s_1^{*T}, s_2^{*T}, s_M^{*T})^T$.

In the third step, seizure detection is conducted to identify the seizure ICs. After applying fast Fourier transform (FFT) to each component, the spectrum power of the jth IC at an empirically defined frequency band (e.g. 5-20 Hz [Reference 3]) can be calculated as follows:

$$P_j = \sum_{k=k_{min}}^{k_{max}} |FFT(s_j^*; k)|^2, \; j=1,2,\ldots,M \qquad (3)$$

where $FFT(s_j^*; k)$ is the kth frequency component for the jth decomposed IC, $k_{mm}$ and $k_{max}$ are the left and right bound of the interested band, $|\cdot|^2$ is the modulus square operation. Two criteria are combined to assure that ICs with strong and fast rhythmic activities are identifiable as seizure components:

1) Spectrum power is higher than a predefined threshold Thres, which is determined by the sampling frequency $F_s$, bandwidth of interest, the number of points in FFT $N_{FFT}$, and a power scaling factor $\alpha$, as shown in equation 4, and
2) Frequency with the largest amplitude or the second largest amplitude locates within the interested band as previously defined. The second one is shown to effectively reduce false detections caused by short paroxysmal activity with large low frequency power.

$$Thres = \alpha^2 \frac{N_{FFT}(k_{max} - k_{min})}{Fs/2} \qquad (4)$$

The criterion-based detection procedure is conducted to each IC sequentially to decide whether it is epileptiform or not. If the jth IC is detected as a seizure source, it is denoted as $s_j^d$. We define a seizure IC matrix $S^d = ((s_{j1}^d)^T, (s_{j2}^d)^T, \ldots, (s_{jR}^d)^T)^T$ including all the detected seizure ICs, where jr is the row number in IC matrix s*.

Finally, to investigate the effects of seizure ICs on recording electrodes, a back projection procedure is performed by incorporating a reduced mixing matrix $A^r$. The reduced mixing matrix is a subset of the matrix A*, which only includes its columns that correspond to the identified seizure IC matrix $s^d$, i.e. $A^r = (a_{j1}, a_{j2}, \ldots, a_{jR})$. Then the back projected data $X^{bp}$ on the original data space can be obtained through computing the product of the reduced mixing matrix and the seizure IC matrix, i.e.

$$x^{bp} = A^r s^d \qquad (5)$$

where
$x^{bp} = ((x_1^{bp})^T, (x_2^{bp})^T, \ldots, (x_N^{bp})^T)^T$, and $x_i^{bp} = (x_i^{bp}(t_1), x_i^{bp}(t_2), \ldots, x_i^{bp}(t_L))^T$.

The power strength $P_n^{bp}$ on each channel can be further calculated by equation 6. The power strength vector $P^{bp} = (P_1^{bp}, P_2^{bp}, \ldots, P_N^{bp})^T$, which is constructed by the power strengths of all channels, can be plotted as the power strength diagram, on which the seizure associated channels could be highlighted.

$$P_n^{bp} = \sum_{t=t_1}^{t_L} |x_n^{bp}(t)|^2, n = 1, 2, \ldots, N \quad (6)$$

Figure 3:
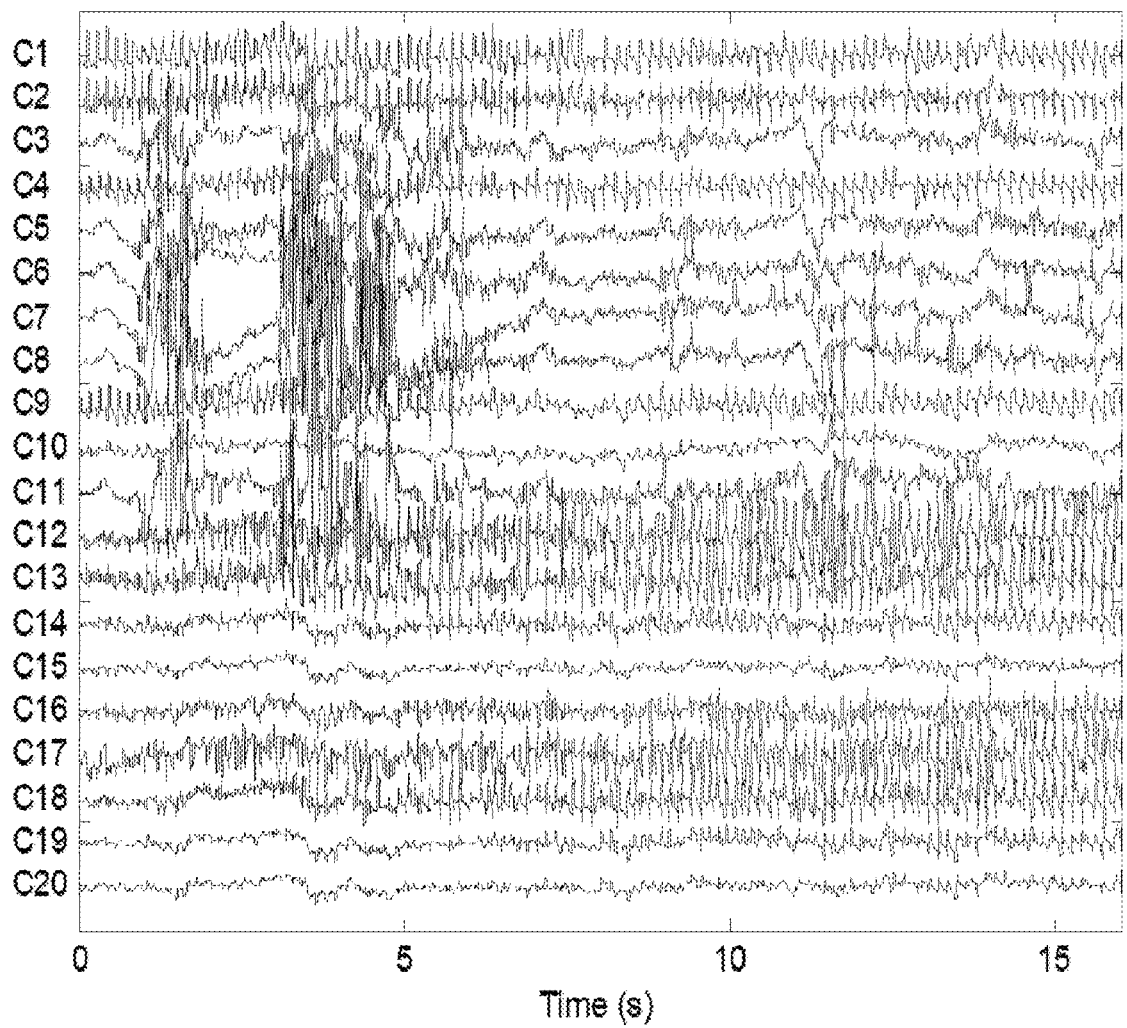
FIG. 3 shows examples of Ictal ECoG waveforms of the 4 by 5 recording channels in one epoch according to an exemplary embodiment of the invention.
Figure 4:
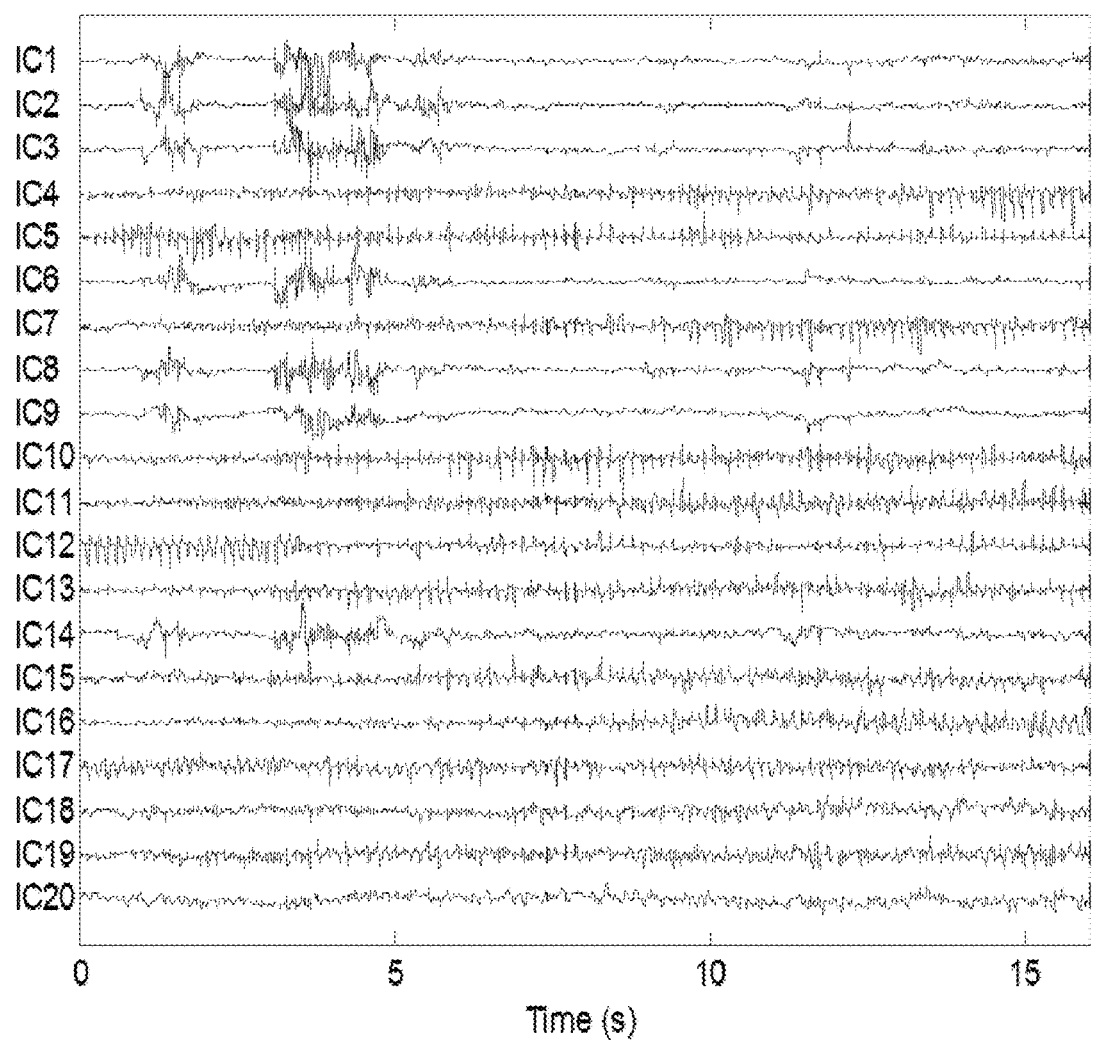
FIG. 4 shows examples of waveforms of decomposed ICs according to an exemplary embodiment of the invention.
Figure 5:
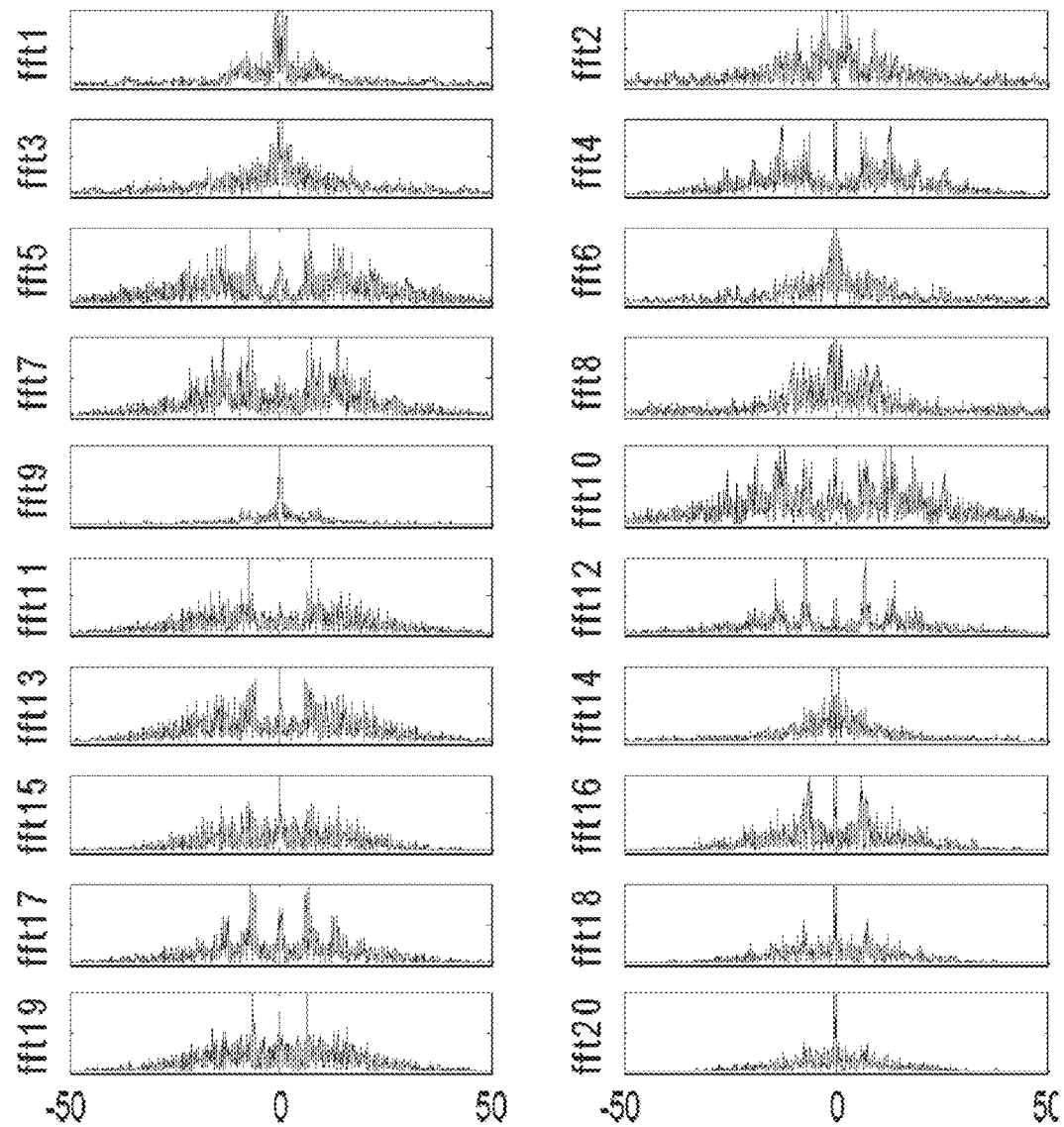
FIG. 5 shows examples of spectra of ICs after FFT according to an exemplary embodiment of the invention. The spectra are plotted up to 50 Hz for an explicit demonstration.

The seizure detection algorithm has been applied and tested by applying nineteen ictal ECoGs and several EEGs from eight patients. All seizures were captured and ictal related channels were identified, which have been verified by epileptologists. As an example, an ictal recording with a 4 by 5 electrode grid from one patient suffering from temporal lobe epilepsy was used to illustrate the whole detection procedure. This recording has 71,000 samples, approximately equivalent to 4.6 minutes at the sampling rate of 256 Hz. An epoch containing 4,096 samples (16 s) was chosen as a base unit for ICA process and seizure detection. This moderate length, avoiding both longer detection latency and less informative data collection, would facilitate the FFT operation in spectrum analysis. The ictal ECoG waveforms of all channels in a selected epoch are shown in FIG. 3. By using ICA, twenty decomposed ICs were extracted from the original signals, as shown in FIG. 4. FIG. 5 shows examples of the spectra of these ICs after utilizing FFT to each IC. Based on the detection criteria, eight ICs were identified as potential seizure sources: IC4, IC5, IC7, IC10, IC11, IC16, IC17, and IC19. FIG. 6A shows the power strength diagram on the electrode array after back projection by incorporating only epileptic components. Compared to FIG. 6B with power strength of the original ECoG data, the strengths of channels with normal activity but strongly interfered by artifacts, for example, C5-C8, were suppressed, and the channels highly involved by epileptic seizures, such as C12, C13, and C17, stand out.

FIG. 7 shows examples of the power strengths of twenty channels vary with time using the same ECoG recording so as to give an idea on the detection accuracy of this method in terms of seizure onset time and involved channels. The waveforms of the recording were visually scored by one epileptologist before we performed the analysis, and the electrographic onset (EO) was marked (EO=120.7 s in this recording). Because all the 16 s samples in each epoch have to be ready to calculate the power strength for a time instant, the time axis in FIG. 7 ranges from 16 s to the end of this recording. Running epochs were used to improve the resolution of power strength diagram with 256 samples (1 s) as each moving step. The power strength diagram of the original ECoG data is shown in FIG. 7A where the black arrow indicates the EO as a reference, and the dotted arrow indicates the selected epoch of the above example. It is found that most of channels express higher power strengths after seizure occurred. However, after performing ICA, seizure detection and back projection on the data, the seizure involved channels are highlighted in FIG. 7B, and the power strengths start to change right after EO. The detection latency approximately equals to one epoch duration. It is noted that if data is analyzed in the offline manner, it is not easy to obtain the "true" latency relative to EO. However, the "true" latency can be estimated as the sum of the latency shown in the power strength diagram and the computational time required for seizure activity detection. The computational time latency becomes negligible as computer technology continues to advance. Thus, the epoch duration, as one of the important parameters in this method, becomes the dominant factor in determining the "true" detection latency.

Source Localization Method

Based on the above described seizure detection method, we further provide a source localization method to localize each seizure source using steepest descent iteration.

First, p principal paths are selected for each seizure IC by choosing p largest absolute elements from the corresponding column of the reduced mixing matrix $A^r$. For the jrth seizure IC, p largest elements are selected from the set $\{|a_{1,jr}|, |a_{2,jr}|, \ldots |a_{N,jr}|\}$ to construct the principal path vector $a_{jr}^P$. The number of principal paths, which can be determined according to the requirements of both localization accuracy and computational load, relates to the number of recording channels that will be used to locate one seizure source. A principal path matrix $A^P$ is obtained by gathering all the principal path vectors, i.e. $A^P = (a_{j1}^P, a_{j2}^P, \ldots, a_{jR}^P)$, where the principal path vector, $a_{jr}^P$, is given by $a_{jr}^P = (|a_{n1,jr}|, |a_{n2,jr}|, \ldots, |a_{np,jr}|)^T$.

Second, a distance matrix $D = (d_{j1}, d_{j2}, \ldots, d_{jR})$ is calculated in the following way. Denote $d_{jr} = (d_{n1,jr}, d_{n2,jr}, \ldots, d_{np,jr})^T$ the principal distance vector. For the jrth seizure IC, the distance between the nith electrode and this underneath source can be estimated using equation 7

$$d_{ni,jr} = \sqrt{\frac{\lambda}{|a_{ni,jr}|}}, i = 1, 2, \ldots, p \quad (7)$$

where $\lambda$ is an empirically selected parameter reflecting the conductivity property of electrophysiological signal transmission through brain tissue. Empirical estimation of parameters could be enhanced with the multi-layers modeling of brain tissue as well as MRI data.

Finally, the steepest descent algorithm is employed to iteratively position the jrth seizure source according to the principal distance vector $d_{jr}$ in the distance matrix. It should be noted that directed transfer function (DTF) could further be introduced to analyze the causal temporal relation among those located seizure sources. Thus the algorithm is able to provide spatial and temporal relationships among the identified seizure onset sources. This would further facilitate the more accurate resection of the epileptogenic lesions.

FIGS. 8A-B demonstrate the estimated locations of eight seizure ICs relative to the mimic human cortex surface in both lateral view and top view. In these figures, the black dots represent the recording electrodes and the other patterns (inside the diamond shapes) are identified sources.

What is claimed is:

1. A method of epileptogenic source localization for obtaining spatial and temporal relationships among epileptogenic zones, comprising:
   (a) performing an Independent Component Analysis (ICA) for seizure detection, wherein said ICA comprises the steps of:
      (i) preprocessing ECoG data obtained using a plurality of channels from a subject's brain, wherein said preprocessing removes the mean of said ECoG data for whitening of said ECoG data;
      (ii) using said preprocessing to uncover Independent Components (ICs) within said ECoG data and to estimate a mixing matrix as a function of said ICs;
      (iii) performing seizure detection on each of said uncovered ICs to identify a seizure, wherein performing seizure detection comprises the steps of:
         (j) applying a fast Fourier transform (FFT) function to each of said ICs to obtain a frequency spectrum of each of said ICs;

(jj) calculating a power spectrum for each of said ICs in a frequency band; and
(jjj) based on one or more criteria, detecting said seizure for each of said ICs, and if said seizure is detected, calculating:
(k) a reduced mixing matrix from said mixing matrix; and
(kk) a seizure IC matrix; and
(iv) performing back projection comprising the steps of:
(p) calculating the product of said reduced mixing matrix and said seizure IC matrix; and
(pp) calculating power strength data for each of said plurality of channels;
(b) performing steepest descent-based source localization for determining temporal relationships among said detected seizures; and
(c) outputting source locations of said detected seizures;
(d) wherein said method of epileptogenic source localization is coded in a computer language and said coded computer language is stored on a computer-readable medium which is executable by a computing device.

2. The method as set forth in claim 1, wherein said one or more criteria for detecting said seizure for each of said ICs comprises one or more of:
(r) a power spectrum being higher than a predefined threshold determined by a sampling frequency, a frequency bandwidth of interest, a number of points in FFT, and a power scaling factor; and
(rr) a frequency with the largest amplitude or a frequency with the second largest amplitude located within said bandwidth of intereste.

3. The method as set forth in claim 1, wherein performing steepest descent-based source localization comprises the steps of:
(s) selecting p principal paths for each of said seizure ICs by choosing p largest absolute elements from a corresponding column of said reduced mixing matrix, wherein the principal paths relate to said plurality of channels;
(ss) calculating a principal distance matrix between said plurality of channels and said sources of said detected seizures;
(sss) applying a steepest-descent algorithm to position each of said sources of said detected seizures according to said principal distance matrix; and
(is) applying a directed transfer function (DTF) to analyze a casual temporal relationship among said sources of said detected seizures.

4. The method as set forth in claim 1, further comprising: displaying said power strength data to a user.

5. An epileptogenic source localization system for obtaining spatial and temporal relationships among epileptogenic zones, comprising:
(a) an ECoG data analysis device for obtaining a plurality of channels from a subject's brain;
(b) a computer processor device for processing a plurality of computer executable modules comprising coded computer language stored on a computer-readable medium which is executable by the computer processor device, wherein a first of said modules comprises an Independent Component Analysis (ICA) module for performing seizure detection, wherein said ICA module is configured for performing the steps of:
(i) preprocessing ECoG data obtained using a plurality of channels from a subject's brain, wherein said preprocessing removes the mean of said ECoG data for whitening of said ECoG data;
(ii) using said preprocessing to uncover Independent Components (ICs) within said ECoG data and to estimate a mixing matrix as a function of said ICs; and
(iii) performing seizure detection on each of said uncovered ICs to identify a seizure, wherein performing seizure detection comprises the steps of:
(j) applying a fast Fourier transform (FFT) function to each of said ICs to obtain a frequency spectrum of each of said ICs;
(jj) calculating a power spectrum for each of said ICs in a frequency band; and
(jjj) based on one or more criteria, detecting said seizure for each of said ICs, and if said seizure is detected, calculating:
(k) a reduced mixing matrix from said mixing matrix; and
(kk) a seizure IC matrix; and
(iv) performing back projection comprising the steps of:
(p) calculating the product of said reduced mixing matrix and said seizure IC matrix; and
(pp) calculating power strength data for each of said plurality of channels; and
(c) wherein a second of said modules comprises a source localization module configured for performing steepest descent-based source localization to determine temporal relationships among said detected seizures and outputting source locations of said detected seizures.

6. The system as set forth in claim 5, wherein said one or more criteria for detecting said seizure for each of said ICs comprises one or more of:
(r) a power spectrum being higher than a predefined threshold determined by a sampling frequency, a frequency bandwidth of interest, a number of points in FFT, and a power scaling factor; and
(rr) a frequency with the largest amplitude or a frequency with the second largest amplitude located within said bandwidth of interest.

7. The system as set forth in claim 5, wherein said source localization module is configured to perform the steps of:
(s) selecting p principal paths for each of said seizure ICs by choosing p largest absolute elements from a corresponding column of said reduced mixing matrix, wherein the principal paths relate to said plurality of channels;
(ss) calculating a principal distance matrix between said plurality of channels and said sources of said detected seizures;
(sss) applying a steepest-descent algorithm to position each of said sources of said detected seizures according to said principal distance matrix; and
(is) applying a directed transfer function (DTF) to analyze a casual temporal relationship among said sources of said detected seizures.

8. The system as set forth in claim 5, wherein said plurality of computer executable modules are further configured to perform the step of:
displaying said power strength data.

* * * * *